United States Patent
Wang et al.

(10) Patent No.: US 7,371,728 B2
(45) Date of Patent: May 13, 2008

(54) PROSTATE-SPECIFIC ANTIGEN PROBES FOR OPTICAL IMAGING

(75) Inventors: Yun-Ming Wang, Kaohsiung (TW); Wei-Hsan Chao, Kaohsiung (TW); Gin-Chung Liu, Kaohsiung (TW); Jui-Sheng Hsu, Kaohsiung (TW)

(73) Assignee: Kaohsiung Medical University, Kaoshiung (TW)

( * ) Notice: Subject to any disclaimer, the term of this patent is extended or adjusted under 35 U.S.C. 154(b) by 0 days.

(21) Appl. No.: 11/325,074

(22) Filed: Jan. 4, 2006

(65) Prior Publication Data

US 2006/0154324 A1 Jul. 13, 2006

(30) Foreign Application Priority Data

Jan. 7, 2005 (TW) .............................. 94100575 A

(51) Int. Cl.
*A61K 38/08* (2006.01)
*C07K 7/04* (2006.01)
*A61K 38/00* (2006.01)
*A61K 38/02* (2006.01)
*C07K 2/00* (2006.01)
*C07K 1/00* (2006.01)

(52) U.S. Cl. ................. 514/15; 514/2; 514/6; 530/300; 530/327; 530/333

(58) Field of Classification Search ..................... None
See application file for complete search history.

(56) References Cited

FOREIGN PATENT DOCUMENTS

WO          WO 00/04391           *     1/2000

* cited by examiner

*Primary Examiner*—Andrew D. Kosar
(74) *Attorney, Agent, or Firm*—Volpe and Koenig, P.C.

(57) ABSTRACT

This invention provides a novel probe, which contains a prostate peptide substrate. The probe can be used as a prostate diagnostic agent for optical imaging. An 11 amino acid peptide substrate is synthesized for specific prostate-specific antigen (PSA). This protected graft copolymer (PGC) consists of a poly-L-lysine (PL) backbone and methoxypoly(ethylene glycol) (MPEG). Two terminals of peptide substrate are bound to poly-L-lysine and Cy5.5 fluorochrome. This probe will be used as a NIR (near-infrared fluorescence) probe for optical imaging.

3 Claims, 7 Drawing Sheets

SEQUENCE LISTING

```
<160> NUMBER OF SEQ ID NOS: 13

<210> SEQ ID NO 1
<211> LENGTH: 9
<212> TYPE: PRT
<213> ORGANISM: Artificial
<220> FEATURE:
<223> OTHER INFORMATION: A nine amino acid peptide substrate
<220> FEATURE:
<221> NAME/KEY: MISC_FEATURE
<222> LOCATION: (2)..(2)
<223> OTHER INFORMATION: Xaa can be a FITC modified Lys residue

<400> SEQUENCE: 1

Cys Xaa Gly Arg Val Gly Leu Pro Gly
1               5

<210> SEQ ID NO 2
<211> LENGTH: 9
<212> TYPE: PRT
<213> ORGANISM: Artificial
<220> FEATURE:
<223> OTHER INFORMATION: A nine amino acid peptide substrate
<220> FEATURE:
<221> NAME/KEY: MISC_FEATURE
<222> LOCATION: (2)..(2)
<223> OTHER INFORMATION: Xaa can be a FITC modified Lys residue

<400> SEQUENCE: 2

Cys Xaa Gly Pro Gly Leu Arg Val Gly
1               5

<210> SEQ ID NO 3
<211> LENGTH: 6
<212> TYPE: PRT
<213> ORGANISM: Artificial
<220> FEATURE:
<223> OTHER INFORMATION: A peptide cutting site

<400> SEQUENCE: 3

Gln Leu Lys Ser Ser His
1               5
```

```
<210> SEQ ID NO 4
<211> LENGTH: 6
<212> TYPE: PRT
<213> ORGANISM: Artificial
<220> FEATURE:
<223> OTHER INFORMATION: A peptide substrated cut site
<220> FEATURE:
<221> NAME/KEY: MISC_FEATURE
<222> LOCATION: (3)..(3)
<223> OTHER INFORMATION: Xaa can be Ile or Lys
<220> FEATURE:
<221> NAME/KEY: MISC_FEATURE
<222> LOCATION: (5)..(5)
<223> OTHER INFORMATION: Xaa can be Leu or Gln

<400> SEQUENCE: 4

Gly Arg Xaa Gly Xaa Pro
1               5

<210> SEQ ID NO 5
<211> LENGTH: 10
<212> TYPE: PRT
<213> ORGANISM: Artificial
<220> FEATURE:
<223> OTHER INFORMATION: A peptide substrate cut site

<400> SEQUENCE: 5

Ala Leu Arg Cys Ser Arg Gln Val Val Gly
1               5                   10

<210> SEQ ID NO 6
<211> LENGTH: 9
<212> TYPE: PRT
<213> ORGANISM: Artificial
<220> FEATURE:
<223> OTHER INFORMATION: A peptide probe

<400> SEQUENCE: 6

Cys Gly Ser Gly Asp Val Glu Asp Gly
1               5

<210> SEQ ID NO 7
<211> LENGTH: 4
<212> TYPE: PRT
<213> ORGANISM: Artificial
<220> FEATURE:
<223> OTHER INFORMATION: A peptide probe cut site

<400> SEQUENCE: 7

Asp Val Glu Asp
1

<210> SEQ ID NO 8
<211> LENGTH: 11
<212> TYPE: PRT
<213> ORGANISM: Artificial
<220> FEATURE:
<223> OTHER INFORMATION: A prostate peptide substrate
<220> FEATURE:
<221> NAME/KEY: MISC_FEATURE
<222> LOCATION: (2)..(2)
<223> OTHER INFORMATION: Xaa is an FITC modified Lys residue
<220> FEATURE:
<221> NAME/KEY: MISC_FEATURE
<222> LOCATION: (7)..(7)
<223> OTHER INFORMATION: Xaa is cyclohexylglycine
<220> FEATURE:
<221> NAME/KEY: MISC_FEATURE
<222> LOCATION: (10)..(10)
<223> OTHER INFORMATION: Xaa is hydroxyproline
```

```
<400> SEQUENCE: 8

Cys Xaa Met Leu Ser Gln Xaa Ser Ala Xaa Gly
1               5                   10

<210> SEQ ID NO 9
<211> LENGTH: 11
<212> TYPE: PRT
<213> ORGANISM: Artificial
<220> FEATURE:
<223> OTHER INFORMATION: A peptide substrate probe
<220> FEATURE:
<221> NAME/KEY: MISC_FEATURE
<222> LOCATION: (1)..(1)
<223> OTHER INFORMATION: Xaa is one selected from the group consisting
      of Cys modified with polysaccharide, polylysine, polyethylene
      imine, and a synthetic polymer
<220> FEATURE:
<221> NAME/KEY: MISC_FEATURE
<222> LOCATION: (2)..(2)
<223> OTHER INFORMATION: Xaa is a FITC modified Lys residue
<220> FEATURE:
<221> NAME/KEY: MISC_FEATURE
<222> LOCATION: (7)..(7)
<223> OTHER INFORMATION: Xaa is cyclohexylglycine
<220> FEATURE:
<221> NAME/KEY: MISC_FEATURE
<222> LOCATION: (10)..(10)
<223> OTHER INFORMATION: Xaa is hydroxyproline
<220> FEATURE:
<221> NAME/KEY: MISC_FEATURE
<222> LOCATION: (11)..(11)
<223> OTHER INFORMATION: Xaa is one selected from the group consisting
      of Gly modified with Cy5.5, Cy5, Cy7, Alexa 750, Alexa 660, Alexa
      680, IR 800, a lanthanide series metal complex, and a near
      infrared fluorescence dye

<400> SEQUENCE: 9

Xaa Xaa Met Leu Ser Gln Xaa Ser Ala Xaa Xaa
1               5                   10

<210> SEQ ID NO 10
<211> LENGTH: 11
<212> TYPE: PRT
<213> ORGANISM: Artificial
<220> FEATURE:
<223> OTHER INFORMATION: A prostate peptide substrate in synthesis
<220> FEATURE:
<221> NAME/KEY: MISC_FEATURE
<222> LOCATION: (1)..(1)
<223> OTHER INFORMATION: Xaa can be Trt modified Cys
<220> FEATURE:
<221> NAME/KEY: MISC_FEATURE
<222> LOCATION: (2)..(2)
<223> OTHER INFORMATION: Xaa can be Dde modified Lys
<220> FEATURE:
<221> NAME/KEY: MISC_FEATURE
<222> LOCATION: (3)..(3)
<223> OTHER INFORMATION: Xaa can be Boc modified Met
<220> FEATURE:
<221> NAME/KEY: MISC_FEATURE
<222> LOCATION: (5)..(5)
<223> OTHER INFORMATION: Xaa can be tBu modified Ser
<220> FEATURE:
<221> NAME/KEY: MISC_FEATURE
<222> LOCATION: (6)..(6)
<223> OTHER INFORMATION: Xaa can be L-Gln
<220> FEATURE:
<221> NAME/KEY: MISC_FEATURE
<222> LOCATION: (7)..(7)
<223> OTHER INFORMATION: Xaa can be cyclohexylglycine
<220> FEATURE:
<221> NAME/KEY: MISC_FEATURE
<222> LOCATION: (8)..(8)
<223> OTHER INFORMATION: Xaa can be tBu modified Ser
```

```
<220> FEATURE:
<221> NAME/KEY: MISC_FEATURE
<222> LOCATION: (10)..(10)
<223> OTHER INFORMATION: Xaa can be tBu modified hydroxyproline
<220> FEATURE:
<221> NAME/KEY: MISC_FEATURE
<222> LOCATION: (11)..(11)
<223> OTHER INFORMATION: Xaa can be t-Boc modified Gly

<400> SEQUENCE: 10

Xaa Xaa Xaa Leu Xaa Xaa Xaa Xaa Ala Xaa Xaa
1               5                   10

<210> SEQ ID NO 11
<211> LENGTH: 11
<212> TYPE: PRT
<213> ORGANISM: Artificial
<220> FEATURE:
<223> OTHER INFORMATION: A prostate peptide substrate in synthesis
<220> FEATURE:
<221> NAME/KEY: MISC_FEATURE
<222> LOCATION: (1)..(1)
<223> OTHER INFORMATION: Xaa can be Trt modified Cys
<220> FEATURE:
<221> NAME/KEY: MISC_FEATURE
<222> LOCATION: (3)..(3)
<223> OTHER INFORMATION: Xaa can be Boc modified Met
<220> FEATURE:
<221> NAME/KEY: MISC_FEATURE
<222> LOCATION: (5)..(5)
<223> OTHER INFORMATION: Xaa can be tBu modified Ser
<220> FEATURE:
<221> NAME/KEY: MISC_FEATURE
<222> LOCATION: (6)..(6)
<223> OTHER INFORMATION: Xaa can be L-Gln
<220> FEATURE:
<221> NAME/KEY: MISC_FEATURE
<222> LOCATION: (7)..(7)
<223> OTHER INFORMATION: Xaa can be cyclohexylglycine
<220> FEATURE:
<221> NAME/KEY: MISC_FEATURE
<222> LOCATION: (8)..(8)
<223> OTHER INFORMATION: Xaa can be tBu modified Ser
<220> FEATURE:
<221> NAME/KEY: MISC_FEATURE
<222> LOCATION: (10)..(10)
<223> OTHER INFORMATION: Xaa can be tBu modified hydroxyproline
<220> FEATURE:
<221> NAME/KEY: MISC_FEATURE
<222> LOCATION: (11)..(11)
<223> OTHER INFORMATION: Xaa can be t-Boc modified Gly

<400> SEQUENCE: 11

Xaa Lys Xaa Leu Xaa Xaa Xaa Xaa Ala Xaa Xaa
1               5                   10

<210> SEQ ID NO 12
<211> LENGTH: 11
<212> TYPE: PRT
<213> ORGANISM: Artificial
<220> FEATURE:
<223> OTHER INFORMATION: A prostate peptide substrate in synthesis
<220> FEATURE:
<221> NAME/KEY: MISC_FEATURE
<222> LOCATION: (1)..(1)
<223> OTHER INFORMATION: Xaa can be Trt modified Cys
<220> FEATURE:
<221> NAME/KEY: MISC_FEATURE
<222> LOCATION: (2)..(2)
<223> OTHER INFORMATION: Xaa can be a FITC modified Lys residue
<220> FEATURE:
<221> NAME/KEY: MISC_FEATURE
<222> LOCATION: (3)..(3)
<223> OTHER INFORMATION: Xaa can be Boc modified Met
<220> FEATURE:
```

```
<221> NAME/KEY: MISC_FEATURE
<222> LOCATION: (5)..(5)
<223> OTHER INFORMATION: Xaa can be tBu modified Ser
<220> FEATURE:
<221> NAME/KEY: MISC_FEATURE
<222> LOCATION: (6)..(6)
<223> OTHER INFORMATION: Xaa can be L-Gln
<220> FEATURE:
<221> NAME/KEY: MISC_FEATURE
<222> LOCATION: (7)..(7)
<223> OTHER INFORMATION: Xaa can be cyclohexylglycine
<220> FEATURE:
<221> NAME/KEY: MISC_FEATURE
<222> LOCATION: (8)..(8)
<223> OTHER INFORMATION: Xaa can be tBu modified Ser
<220> FEATURE:
<221> NAME/KEY: MISC_FEATURE
<222> LOCATION: (10)..(10)
<223> OTHER INFORMATION: Xaa can be tBu modified hydroxyproline
<220> FEATURE:
<221> NAME/KEY: MISC_FEATURE
<222> LOCATION: (11)..(11)
<223> OTHER INFORMATION: Xaa can be t-Boc modified Gly

<400> SEQUENCE: 12

Xaa Xaa Xaa Leu Xaa Xaa Xaa Xaa Ala Xaa Xaa
1               5                   10

<210> SEQ ID NO 13
<211> LENGTH: 11
<212> TYPE: PRT
<213> ORGANISM: Artificial
<220> FEATURE:
<223> OTHER INFORMATION: A prostate peptide substrate in synthesis
<220> FEATURE:
<221> NAME/KEY: MISC_FEATURE
<222> LOCATION: (2)..(2)
<223> OTHER INFORMATION: Xaa can be a FITC modified Lys residue
<220> FEATURE:
<221> NAME/KEY: MISC_FEATURE
<222> LOCATION: (6)..(6)
<223> OTHER INFORMATION: Xaa can be L-Gln
<220> FEATURE:
<221> NAME/KEY: MISC_FEATURE
<222> LOCATION: (7)..(7)
<223> OTHER INFORMATION: Xaa can be cyclohexylglycine
<220> FEATURE:
<221> NAME/KEY: MISC_FEATURE
<222> LOCATION: (10)..(10)
<223> OTHER INFORMATION: Xaa can be hydroxyproline

<400> SEQUENCE: 13

Cys Xaa Met Leu Ser Xaa Xaa Ser Ala Xaa Gly
1               5                   10
```

US 7,371,728 B2

PROSTATE-SPECIFIC ANTIGEN PROBES FOR OPTICAL IMAGING

FIELD OF THE INVENTION

The present invention relates to an peptide compound of prostate optical probe in which a protected graft copolymer (PGC) consists of a poly-L-lysine (PL) backbone and methoxypoly(ethylene glycol) (MPEG) and that two terminals of peptide substrate are bound to poly-L-lysine and Cy5.5 fluorochrome, particularly to one used as a probe for optical imaging by using the prostate peptide substrate.

BACKGROUND OF THE INVENTION

In the literatures, two terminals of a specific peptide substrate are respectively bound to poly-L-lysine (PL) and fluorochrome. In the other method, two terminals of a peptide substrate are covalently bound to fluorochrome and quencher of the fluorochrome.

Recently, because the developments of hardware and software of optical imaging, the diagnosis of optical imaging improves. In order to enhance the sensitivity and accuracy of the diagnosis of optical imaging, to develop a safe stable targeting probe for optical imaging becomes an important subject of current optical imaging research. A general probe for optical imaging is formed by respectively bonding two terminals of a peptide substrate to a portion of amino acids of poly-L-lysine (PL) and fluorochrome Cy5.5.

Molecular imaging contains magnetic resonance imaging (MRI), nuclear medicine and optical imaging. After the developments in techniques of magnetic resonance imaging, nuclear medicine and optical imaging, in the past ten years, the study and research of in-vivo molecular imaging are rapidly developing and growing. The in-vivo molecular imaging can provide observation and information of an in-vivo biology system at molecular and genetic function level including normal and abnormal cell process. The observation and information are used in the early diagnosis and genomic medicine and rapid development of new medicine of human diseases. The medicines needed by the three imaging instruments shall mainly have biological activity and targeting. For a general conventional medical imaging technique, the conditions of disease during a long-term, such as the size of tumor, are reflected and output only. By using molecular imaging, the short-term biological mutations, such as pre-cancer molecular change, cancer cell short-term transplant, cardiovascular preliminary fibrosis, etc., can be detected. Thus, the molecular imaging is the best early diagnostic method for tumors, coronary disease and chest diseases which threaten the life of human beings. In in-vivo molecular imaging field, the study fields of molecular biology, chemistry, physics, radiotherapeutics, nuclear medicine and computer science are combined because in-vivo imaging can be obtained by contributions of core techniques of each study field. After the recent development of in-vivo molecular imaging was carried out for several years, molecular imaging is superior by comparing to general conventional medical imaging. Many researches were directed to the reaction mechanism and cell composition of disease molecule. The main efforts of them are directed to noninvasive in-vivo imaging technique of high resolution. After the nuclear medicine imaging and magnetic resonance imaging based on human anatomy and pathology are compared to optical imaging, it is known that molecular imaging has entered the threshold of biology molecule calculated by unit of nano meter. Therefore, the early diagnosis and monitor of a disease are studied by gene level, the results and techniques of the study can be intensively applied to biology and disease therapeutics.

Typical fluorochromes use fluorescence having wavelength in visible light range of 400-600 nm. The fluorescence signal of the fluorochromes can be seen by spectrophotometer or fluorescence microscope. But, the photons in this wavelength range are not well used in in-vivo or in-vitro application because tissues and blood will absorb the photons having the wavelength. Recently, fluorescence is used in labeling antibodies, DNA probes, biochemical analogs, lipids, medicaments, cell compositions and polymers. The fluorescence will be suitable for applying in detector and useful as light source after brightness of the fluorescence is enhanced, the light stability of it is increased, the toxicity is decreased, the non-specific bondage is lowered and the excitation and emitting wavelength become better.

The current direction and field of the study and application of molecular imaging include research of small animal imaging technique and development of new molecular probes, and research and study of imaging of in-vivo cell behavior and animal mode including gene expression, receptor and transporter, angiogenesis, drug resistance, drug abuse and targeted radionuclide therapy.

The subject was that after activation by an enzyme, a biocompatible near-infrared fluorescence imaging probe having light inhibition effect could generate a stronger signal and was designed into two kinds. One was a fluorescence supplier and the other was a quencher which was directly bound to two terminals of peptide substrate (G. Zlokarnik et al, Science, 1998, vol 279, page 84; S. V. Gulnik et al, FEBS LETT, 1997, vol 413, Page 379). The quencher was like to use a protected graft copolymer (PGC) which could help to inhibit a propagation of a tumor which was labeled by a near-infrared fluorescence probe and which was used in clinical test (R. Callahan et al, 1998, Am. J. Roentgenol. vol 171, page 137; C. H. Tung et al, 2000. Cancer Research, vol 60, page 4953).

A new near-infrared fluorescence (NIRF) probe generates an in-vivo image after activation by an enzyme. When the probe is not activated by the enzyme, the probe has self-quench effect and can not emit near-infrared light. When enzyme activates the probe, the self-quench effect diminishes and the probe can generate fluorescence light after activated by light.

The design for a general probe has several requisite properties, thus, the probe must has the following properties, such as, a longer recycle time, a high tumor accumulation. The probe was activated to emit a near-infrared fluorescence. The composition of the probe was formed by binding of an amino group at an upper portion of a poly-L-lysine (PL) backbone to methoxypoly(ethylene glycol) (MPEG) and binding of an amino acid sequences to an amino group at the other portion of the poly-L-lysine (PL) backbone with the other terminal of the amino acid sequences being bound to Cy5.5 dye so as to produce the so-called near-infrared fluorescence probe (see, U. Mahmood et al, 1999, Radiology, vol 213, page 866). In view of application of optical imaging to biological imaging, when an enzyme cut a near-infrared fluorescence probe, the probe was light-activated to generate a near-infrared fluorescence (NIR, $\lambda=680$-900 nm). Before the enzyme cut the probe, the probe had self-quench effect not to emit near-infrared fluorescence. Regarding in-vivo imaging, the probe provided relative superiority within near-infrared range (700-1000 nm). For example, water and most of the existing fluorochromes absorb the light energy within near-infrared range. Therefore, within infrared range emissions within near-infrared range it penetrated tissues more efficiently than that of visible light or photons. An ideal near-infrared fluorochrome for in-vivo imaging shall have the following features: (1) A peak of fluorescence shall be within 700-900 nm, (2) high quantum yield, (3) narrow excitation and emission spectrum, (4) chemical and light stability, (5) low toxicity, (6) biocompatibility, biodegradation and emission capability, (7) a few mono-functional derivatives can be obtained (8) commercial feasibility.

The images obtained by use of a probe with respect to different proteases were designed as disclosed in R. Weissleder et al, 2001, Nat. Med., vol 7, page 743. US 2003/0219383A1 disclosed two species of different peptides obtained and synthesized with respect to matrix metalloprotease 2 (MMP-2). One of the probe peptide structures was a peptide substrate Gly-Pro-Leu-Gly-Val-Arg-Gly-Lys (FITC)-Cys-NH2 [SEQ ID NO: 1] with the other being a control peptide Gly-Val-Arg-Leu-Gly-Pro-Gly-Lys(FITC)-Cys-NH2 [SEQ ID NO: 2]. The cutting sites of the enzyme in U.S. Pat. application 2003/0219383A1 were (1) Lys●Lys, (2) PIC(Et)Phe●Phe, (3) His-Ser-Ser-Lys-Leu-Glne●[SEQ ID NO: 3], (4) Pro(Leu/Gln)Gly●(Ile/Lys)Arg-Gly [SEQ ID NO: 4], (5) Gly-Val-Val-Gin-Arge●Ser-Cys-Arg-Leu-Ala [SEQ ID NO: 5].

It was proved by a high performance liquid chromatography (HPLC) that an enzyme of matrix metalloprotease 2 (MMP-2) had the capability of cutting at Gly-Val residue while the control peptide could not be cut by the enzyme. The main purpose of an addition of fluorescein isothiocyanate (FITC) was used as a tag to measure amount of fluorescence and used to bind a thio group of cysteine of the peptide substrate to an amino group of a poly-L-lysine and to flurorchrome, to be used as a probe of matrix metalloprotease 2 (MMP-2).

A design of a probe for thrombin was disclosed in C.H. Tung et al, 2002, ChemBioChem., vol 3, page 207. One of the probe structures of the thrombin probe was a blood coagulation peptide substrate Gly-(D-Phe)-Pip-Arg-Ser-Gly-Gly-Gly-Gly-Lys(FITC)-Cys-NH$_2$ while the other was a control peptide Gly-(D-Phe)-Pip-Arg-Pro-Gly-Gly-Gly-Gly-Lys(FITC)-Cys-NH$_2$. By using a high performance liquid chromatography, it was judged and confirmed that the thrombin enzyme had capability of activate on Arg-Ser residue and that the control peptide had no activation effect on thrombin. It was disclosed in C.H. Tung et al., 2002, Angew. Chem., vol 114, page 3811 that a near--infrared fluorescence inhibitor of an azulene dimmer was synthesized and that a carboxyl group terminal was bound to a peptide sequence, i.e. Gly-Asp-Glu-Val-Asp-Gly-Ser-Gly-Cys [SEQ ID NO: 6] and the other Cys terminal was bound to a fluorochrome so as to emit near-infrared fluorescence. The peptide sequence could cut Asp-Glu-Val-Asp [SEQ ID NO: 7] residue by using capase-3.

It was disclosed in C. H. Tung et al, 2003, Tetrahedron Letters., vol 44, page 3975 a near-infrared quencher (NIRQ$_{700}$) of mono-functional azulenyl squarain dye was synthesized and its wavelength absorption was within 600-700 nm. The wavelength absorption revealed that the probe could be effectively used as a quencher toward a fluorochrome within 600-750 nm.

The application of hormone-inhibitor (somatostatine) receptor to diagnosis and treatment was disclosed in K. Licha et al, 2001, Bioconjugate Chen., vol 12, page 44. A peptide-N-terminal amino functional group of a receptor-specific somatostatine was bound to an indodicarbocyanine (IDCC) and indotricarbocyanine (ITCC). The probe showed that it had a better molar absorption coefficient and fluorescence quantum yield. The results proved that the probe could emit near-infrared fluorescence and the probe was suitable for application as a probe of receptor-targeted molecular imaging.

It was disclosed in A. Becke et al, 2001, Nature Biotechnology, vol 19, page 327 that a cyanine dye derivative was bound to a hormone receptor antagonist (octreotate) peptide derivative useful as a probe of optical imaging. Its in-vivo images showed that the peptide effect was best when indodicarbocyanine (IDCC) was bound to hormone receptor antagonist (octreotate).

It was disclosed in C. H. Tung et al, 2002, ChemBioChem, vol 8, page 784 that a small molecular probe was used to emit near-infrared fluorescence (NIRF: 700-900 nm), for the targeted compound of fluorescence molecular imaging the small molecular probe was especially bound to a peptide and a fluorochrome. The results demonstrated that in the in-vivo optical image the probe was targeted to folate receptor in order to detect many forms of tumors, especially ovarian cancer. Therefore, the small molecular probe had a better medicine kinetics and non-immunity property.

From the results of the above literatures, it was shown that probes were designed to be used on various proteases. In the present invention, an optical imaging probe obtained by binding a peptide to near-infrared fluorochrome (Cy5.5) to form a bioconjugate. The present invention provides a prostate peptide substrate designed for a prostate-specific antigen enzyme, which is Gly-Hyp-Ala-Ser-Chg-Gln-Ser-Leu-Met-Lys(FITC)-Cys-NH$_2$ [SEQ ID NO: 8]. Methoxypoly(ethylene glycol) (MPEG) is bound to an amino group at upper portion of poly-L-lysine (PL) and two terminals of the designed amino acid sequences are respectively bound to poly-L-lysine (PL) and Cy5.5 dye to form a near-infrared fluorescence probe. The specificity of the prostate-specific antigen enzyme is studied.

The cyclohexyl-gly (Chg) is an amino acid having the following formula:

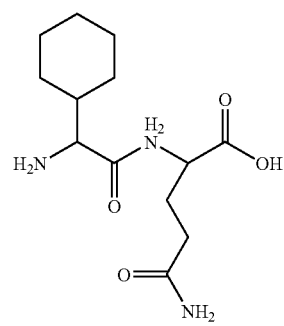

SUMMARY OF THE INVENTION

It is a first aspect of the present invention to provide a protected graft copolymer (PGC) consisted of a poly-L-Lysine (PL) backbone and methoxypoly(ethylene glycol) (MPEG). Two terminals of a peptide substrate are bound to poly-L-Lysine and Cy5.5 fluorochrome. The probe will be used as a NIR (near-infrared fluorescence) probe for optical imaging.

It is another aspect of the present invention to provide a prostate peptide substrate and an optical imaging probe for diagnosing prostatic cancer.

It is another aspect of the present invention to provide a peptide compound of the prostatic optical imaging probe and a method for its preparation.

It is another aspect of the present invention to provide a prostate peptide substrate having the following formula:

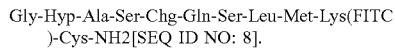
Gly-Hyp-Ala-Ser-Chg-Gln-Ser-Leu-Met-Lys(FITC)-Cys-NH2[SEQ ID NO: 8].

It is another aspect of the present invention to provide a peptide substrate probe having the following formula (I):

B-Gly-Hyp-Ala-Ser-Chg-Gln-Ser-Leu-Met-Lys(FITC)-Cys-P [SEQ ID NO: 9]  (I)

wherein,

B is one selected from the group consisting of Cy5.5, Cy5, Cy7, Alexa 750, Alexa 660, Alexa 680, IR 800, a lanthanide series metal complex and a near-infrared fluorescence dye;

P is one selected from the group consisting of a polysaccharide, a polylysine, a polyethylene imine and a synthetic polymer.

Preferably, the peptide substrate probe is used as a prostate diagnostic agent for optical imaging.

Preferably, the peptide substrate probe can be cut by a prostate-specific antigen.

It is another aspect of the present invention to provide a method for diagnosing a human prostatic cancer comprising the steps of:
(a) synthesizing a prostate peptide substrate and a control peptide;
(b) synthesizing a prostate peptide substrate probe and a prostate control peptide probe; and
(c) diagnosing the human prostatic cancer with the prostate peptide substrate probe and the prostate control peptide probe.

Preferably, the diagnosing is achieved through a preparation of a prostate diagnostic agent for optical imaging.

It is another aspect of the present invention to provide a prostatic cancer probe as stated above useful for diagnosing an in-vivo prostatic cancer through a preparation of a prostate diagnostic agent for optical imaging.

The foregoing and other features and advantages of the present invention will be more clearly understood through the following descriptions with reference to the drawings, wherein:

DETAILED DESCRIPTION OF THE PREFERRED EMBODIMENT

Figure 1:
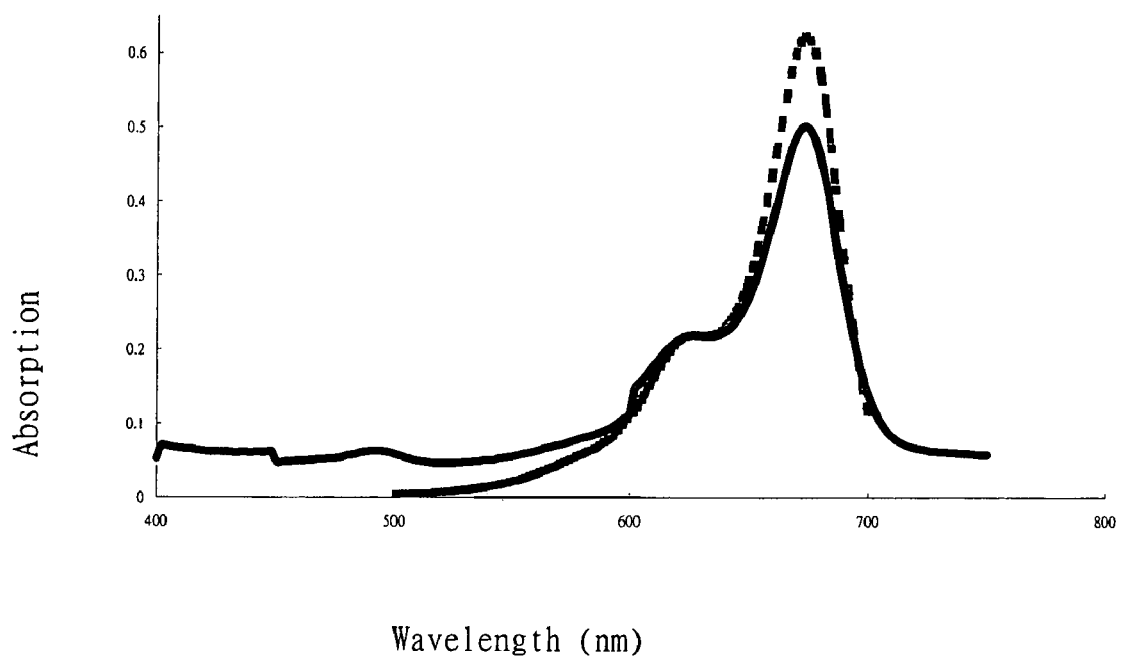
FIG. 1 is a UV/Vis absorption spectrum diagram showing relationship of FITC (grey line), Cy5.5 (dot line) and Cy5.5-prostate-PGC (solid line) of the present invention.

Recently the subject to be studied is to develop a biologically active and highly stable peptide compound. Until now, those skilled in the art still make efforts to research and find excellent optical imaging probes. Therefore, the purpose of the present invention is to synthesize a promising, novel, stable and biologically active peptide compound to be used as an optical imaging probe.

In order to achieve the object of the present invention, the present invention provide a synthesized prostate peptide substrate having the following formula (A):

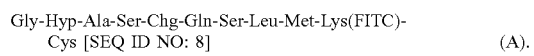
Gly-Hyp-Ala-Ser-Chg-Gln-Ser-Leu-Met-Lys(FITC)-Cys [SEQ ID NO: 8]  (A).

The present invention provides a novel probe which is of the synthesized prostate peptide substrate (A) which is consisted of 11 amino acids which is specific toward prostate-specific antigen (PSA) enzyme. The 11 amino acids without FITC was disclosed in D. A. Armbruster, 1966, Clin. Chem., vol 71, page 328, B. K. Wong et al, 2001, Pharmacol, vol 29, page 313, R. S. Dipaola et al, 2002, Journal of Clinical Oncology, vol 20, page 1874, V. M. Garsky, 2000, Nat. Med., vol 6, page 1248. The probe is specific toward Gln-Ser residue and this peptide substrate has been applied to the treatment of prostatic cancer.

The present invention provides an optical imaging probe for detecting prostatic cancer having the following formula (I):

B-Gly-Hyp-Ala-Ser-Chg-Gln-Ser-Leu-Met-Lys(FITC)-Cys-P [SEQ ID NO: 9]  (I).

A protected graft copolymer (PGC) consisted of a poly-L-Lysine (PL) backbone and methoxypoly(ethylene glycol) (MPEG). Two terminals of peptide substrate are bound to poly-L-lysing and Cy5.5 fluorochrome. The probe will be used as a NIR (near-infrared fluorescence) probe for optical imaging in which B is one selected from the group consisting of Cy5.5, Cy5, Cy7, Alexa 750, Alexa 660, Alexa 680, IR 800, a lanthanide series metal complex and a near-infrared fluorescence dye; P is one selected from the group consisting of a polysaccharide, a polylysine, a polyethylene imine and a synthetic polymer.

As described in the following examples, the present invention succeeds to synthesize a prostate optical imaging probe having the following formula (B)

B-Gly-Hyp-Ala-Ser-Chg-Gln-PSA-Ser-Leu-Met-Lys
(FITC)-Cys-P [SEQ ID NO: 9]         (B)

The inventor expects the synthesized optical imaging probe has the following properties:
1. high selectivity toward an optical imaging peptide substrate;
2. to activate peptide substrate by an enzyme to be a better targeted probe;
3. to be targeted probe because it contains a peptide.

The prostate peptide substrate probe of the present invention can be used as an optical imaging probe and has the formula (I).

The method for synthesizing methoxypoly(ethylene glycol) succinimidyl propionic acid (MPEG-SPA) (5) was disclosed in U.S. Pat. No. 5,672,622 as shown in the following Scheme 1:

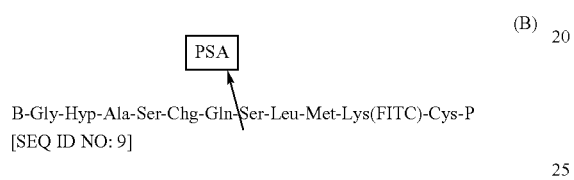

B-Gly-Hyp-Ala-Ser-Chg-Gln-Ser-Leu-Met-Lys(FITC)-Cys-P
[SEQ ID NO: 9]

The method for synthesizing prostate peptide substrate and its control peptide is shown in the following Scheme 2:

Scheme 2: Synthesis diagram of prostate peptide substrate and control peptide

[SEQ ID NO: 10]

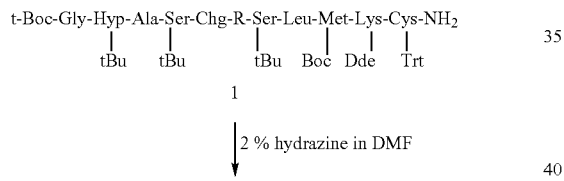

2 % hydrazine in DMF

[SEQ ID NO: 11]

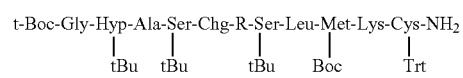

4 eq FITC
DMSO/diisopropylethylamine
(20%v/v, 5ml)

[SEQ ID NO: 12]

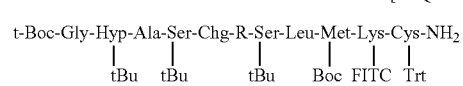

TFA/water/EDT/TIS
94.5/2.5/2.5/1

[SEQ ID NO: 13]

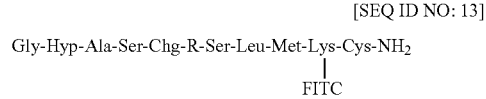

Identified by C18 reversed phase HPLC using 1% TEA and MeOH as elution buffer.

[SEQ ID NO: 8]

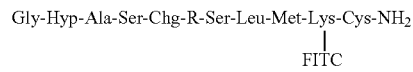

R = L-Gln(Trt) is a prostate peptide substrate
R = D-Gln(Trt) is a control peptide Scheme 3 Synthesis diagram of prostate peptide substrate optical imaging probe (Cy-prostate-PGC) and prostate control peptide probe

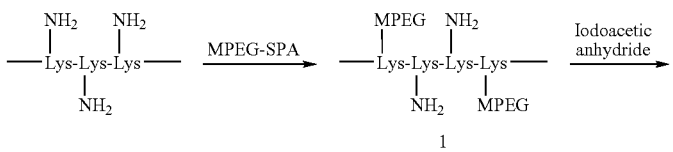

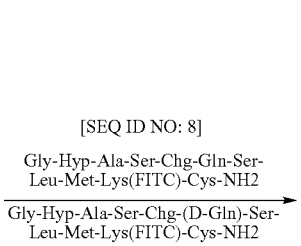

[SEQ ID NO: 8]
Gly-Hyp-Ala-Ser-Chg-Gln-Ser-Leu-Met-Lys(FITC)-Cys-NH2
Gly-Hyp-Ala-Ser-Chg-(D-Gln)-Ser-Leu-Met-Lys(FITC)-Cys-NH2

-continued

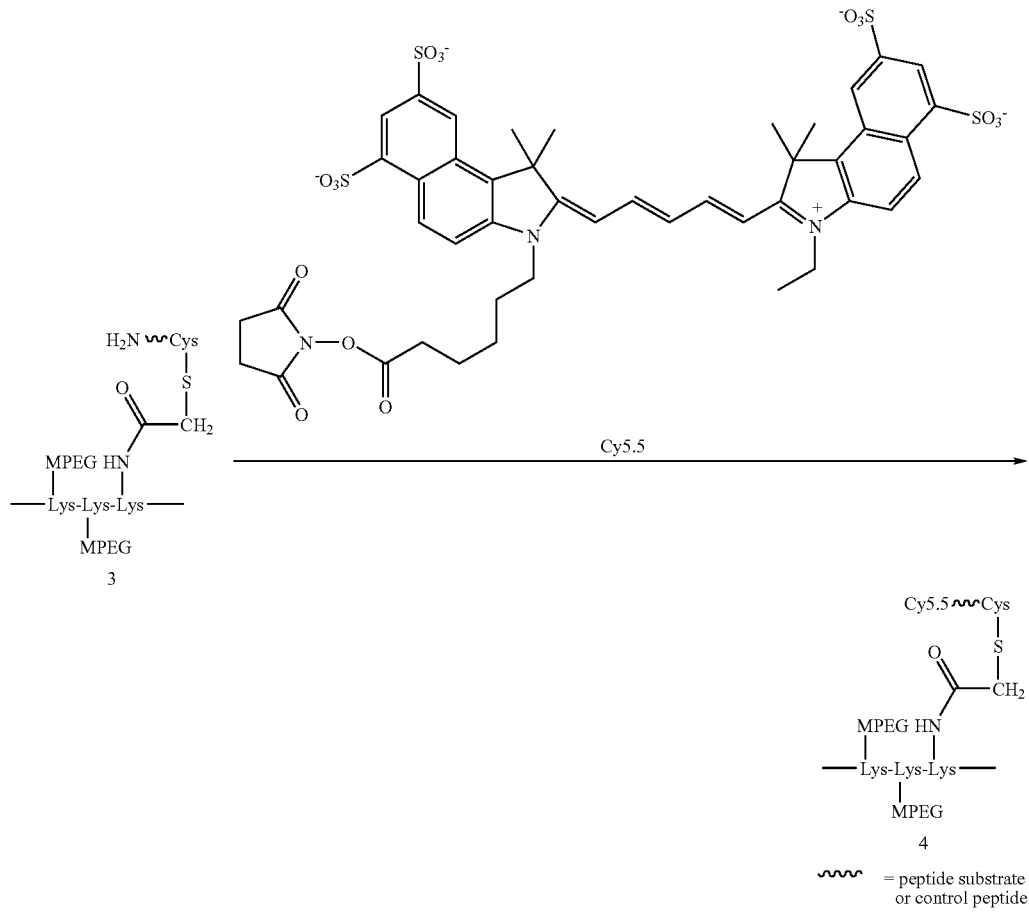

ᴡᴡᴡ = peptide substrate or control peptide

Survey of Biologically Active Optical Imaging Probe:

Two terminals of the prostate peptide substrate of the present invention are respectively bound to poly-L-lysine and fluorochrome to form a biologically active compound as an optical imaging probe.

Figure 2:
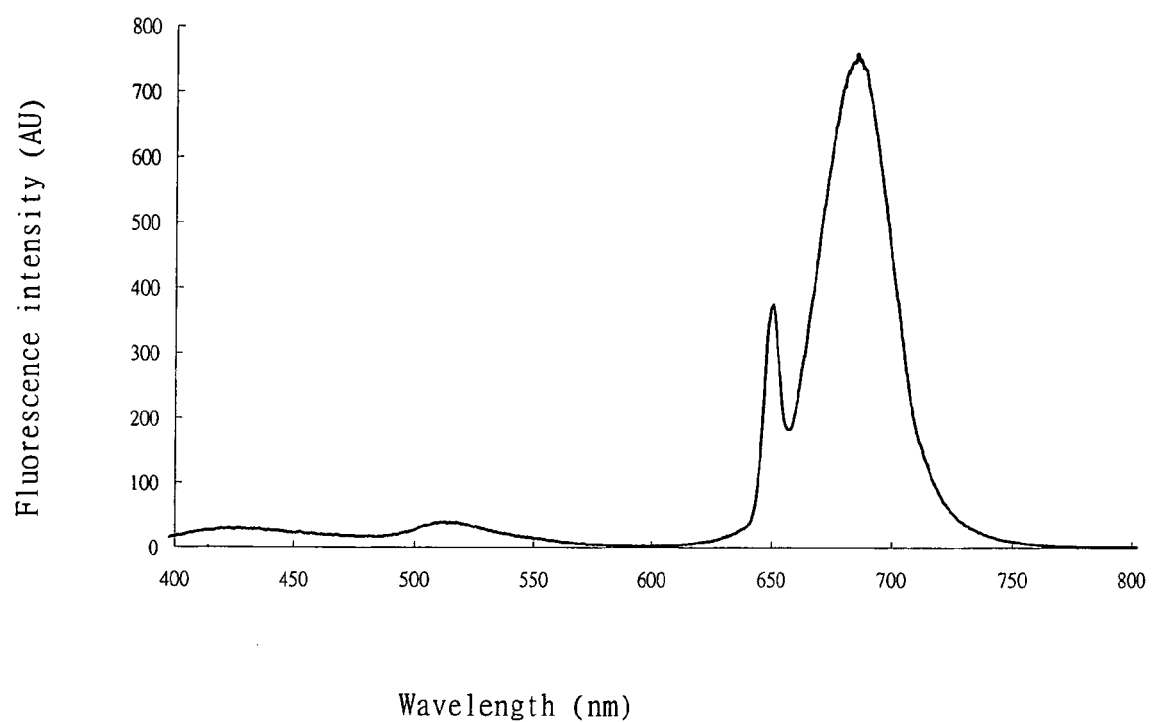
FIG. 2 is a diagram of fluorescence absorption spectrum of prostate probe Cy5.5-prostate-PGC of the present invention.

The analytic results of UV/Vis spectrum of the probe is shown in FIG. 1. The maximum absorption wavelength for FITC and Cy5.5 are 494 and 647 nm, respectively. The analytic results of fluorescence spectrum is shown in FIG. 2. The maximum excitation/emission wavelength for FITC and Cy5.5 are respectively 485/517 and 650/686 nm.

The Study of Peptide Specificity for Prostate-Specific Antigen:

The high performance liquid chromatography is used for application in study of peptide separation, peptide purity analysis and specific enzyme-cutting specificity for a peptide substrate. In in-vivo molecular image, the purity of the peptide is required to reach to 99% or more revealed by literature study so as to obtain an excellent optical image. The goal of the study of the present invention is to develop prostate peptide substrates and enzymes by in-vitro experiments.

Figure 3:
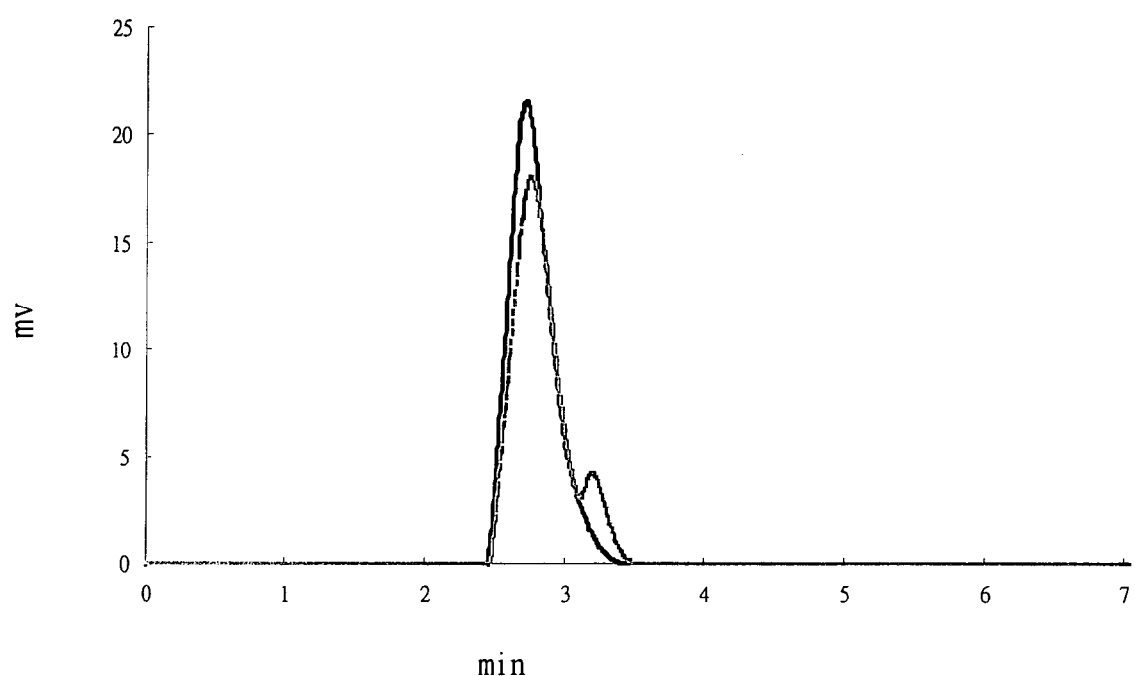
FIG. 3 is a high performance liquid chromatography (HPLC) diagram showing a prostate peptide substrate (0.64 μmol) of solid line and a prostate peptide substrate in the presence of a prostate-specific antigen of grey line of the present invention.
Figure 4:
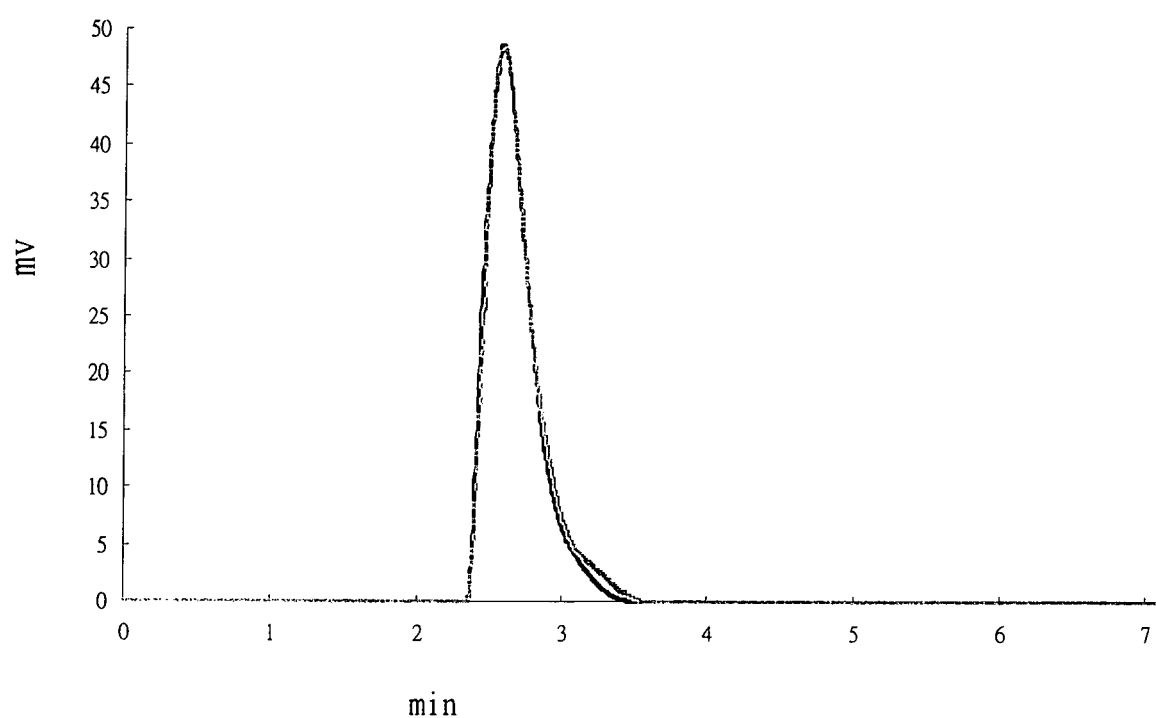
FIG. 4 is a high performance liquid chromatography (HPLC) diagram showing a prostate control peptide (0.64 μmol) of solid line and a prostate control peptide in the presence of a prostate-specific antigen of grey line of the present invention.

The chromatographic diagrams of specificity analysis of the prostate peptide substrates and prostate-specific antigen are shown in FIGS. 3 and 4. The conditions of the HPLC are as follows: a reverse C18 chromatography column, mobile phase is methyl alcohol: 1% triethylamine=60:40(v/v), flow rate is 0.5 ml/min. After detection at 480/525 nm of excitation/emission wavelength by fluorescence detector, it is demonstrated that the prostate peptide substrate can cut Gln-Ser residue in the presence of the prostate-specific antigen enzyme. By spectrums of HPLC, the retention time of the prostate peptide substrate is demonstrated to be 2.7 min as shown in FIG. 3. There are two peaks in the spectrums if HPLC runs in the presence of the prostate-specific antigen with the retention times being 2.7 and 3.2 min as shown in FIG. 3. The chromatographic spectrum shows that in the absence of the prostate-specific antigen for control peptide and in the presence of prostate-specific antigen enzyme, the original peak remains with the retention time being 2.6 min as shown in FIG. 4.

Figure 5:
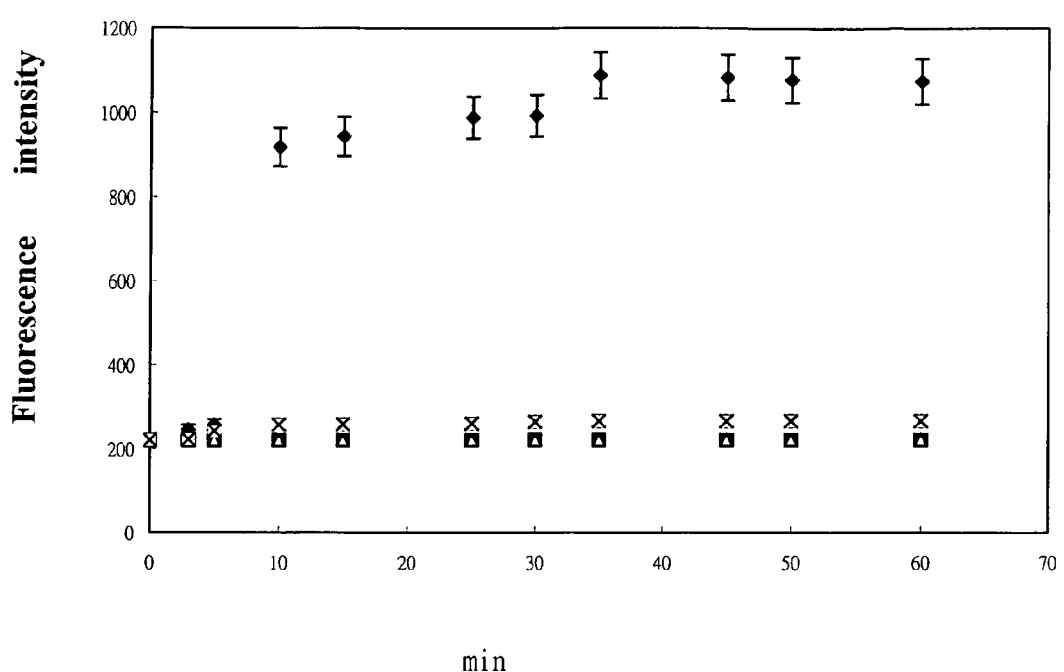
FIG. 5. is a fluorescence absorption verse time diagram showing fluorescence intensity of a control peptide probe (×) for a prostate peptide substrate probe Cy-prostate-PGC (■), control peptide probe (Δ) and a prostate peptide probe in the presence of a prostate-specific antigen (♦) according to the present invention.

The Study for Quenching and Non-Quenching of a Enzyme:

At different time, a prostate peptide substrate and prostate control peptide are reacted with an enzyme of prostate-specific antigen to record its fluorescence spectrum and the results are shown in FIG. 5. From the fluorescence spectrum, it is found that the fluorescence intensity of the original probe is smallest. When the reaction time for the reaction between prostate peptide substrate and the prostate-specific antigen reaches 35 minutes and the signal intensity becomes 5 times as that of the original fluorescence intensity. It shall be noted that the fluorescence intensity of the prostate control peptide in the presence of the prostate-specific antigen and under the same reaction conditions increases less than one time of the original one.

Figure 6:
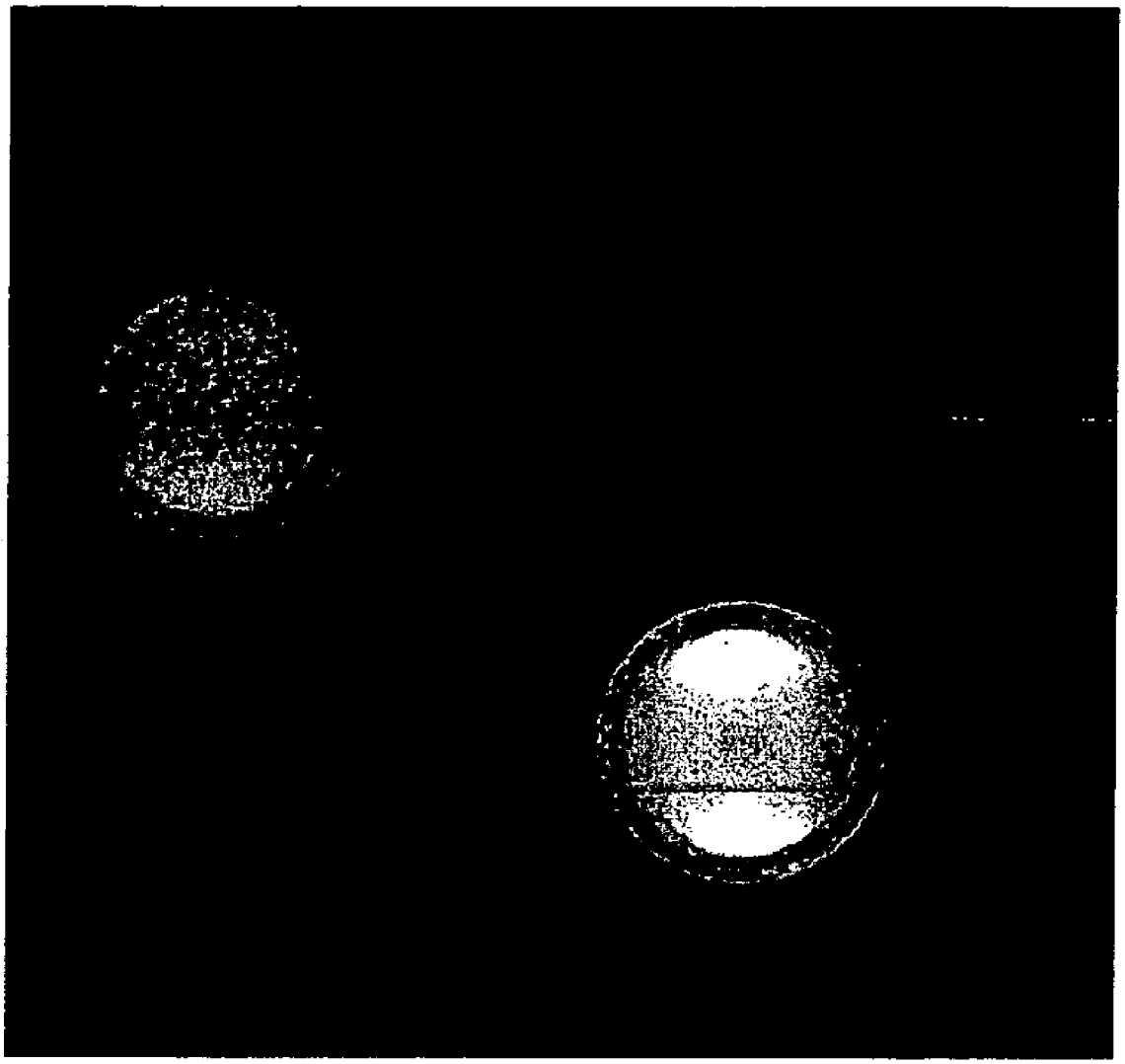
FIG. 6. is optical image (optical image system is 605-645 nm filter and 680-720 nm radiation filter) showing reaction between control peptide probe and prostatic cancer cell lines of human beings and reaction between prostate peptide substrate probe and prostatic cancer cell lines of human beings according to the present invention.

Study of In-Vitro and In-Vivo Optical Imaging:

After a human prostatic cancer cell line is reacted with a control peptide probe and a prostate peptide substrate probe respectively by using an optical imaging scanner to get an image, the results are shown in FIG. 6. The results revealed that the signal intensity for the prostate peptide substrate probe is significant stronger than that for the control peptide probe. This implies that the fluorescence intensity of the prostate peptide substrate enhances after the prostate-specific antigen for the prostatic cancer cell line obviously cuts the prostate peptide substrate.

Figure 7:
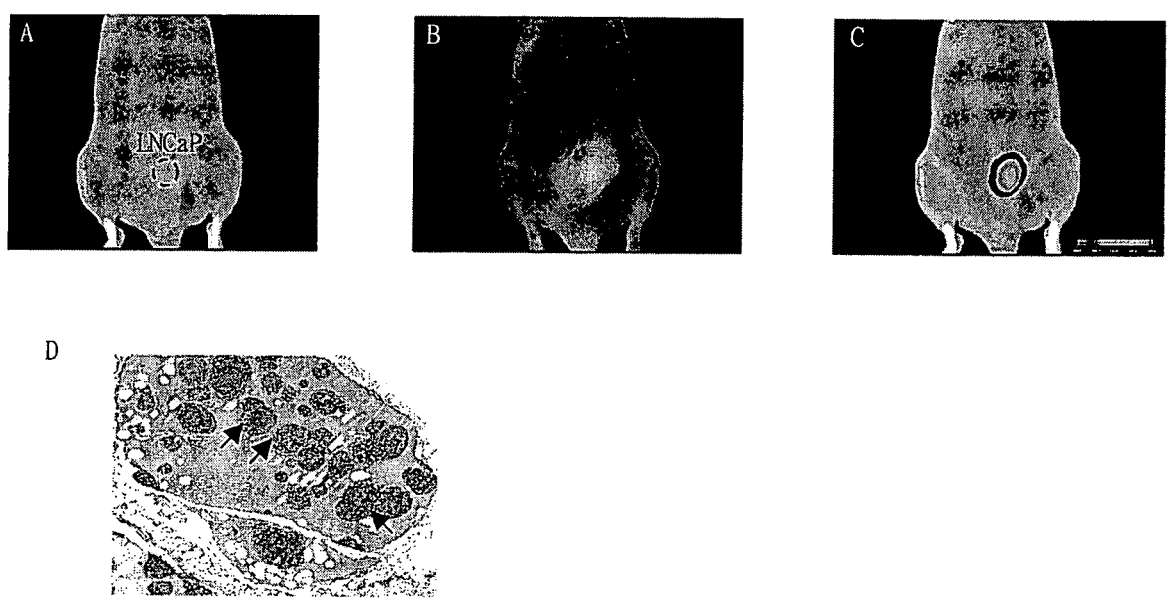
FIG. 7. is optical image (optical image system is 605-645 nm filter and 680-720 nm filter) showing white light image (A), near-infrared fluorescence image (B) and color-coded image (C) obtained in a nude mouse shows significant enhancement of tumor measured an approximately 3 mm in diameter 15 mins after injection of 2 nmol PSA-sensitive probe (Cy-prostate-PGC). Histological specimen (D) demonstrates poorly differentiated LNCaP cells. (Hematoxylin-eosin, ×100, original magnification)

In vivo image studies, clearly detectable NIRF signals were observed from all prostate tumors in live animals, and a representative image sequence was shown in FIG. 7. White light image (A), near-infrared fluorescence image (B) and color-coded image (C) obtained in a nude mouse shows significant enhancement of tumor measured an approximately 3 mm in diameter 15 mins after injection of 2 nmol PSA-sensitive probe (Cy-prostate-PGC). Histological specimen (D) demonstrates poorly differentiated LNCaP cells. (Hematoxylin-eosin, ×100, original magnification)

The mean signal intensity of the prostate tumor 15 minutes after injection was $1.41\times10^4\pm0.28$ (AU). Histological specimens demonstrate poorly differentiated LNCaP cells. Signal that arises from the tumor is due to activation of the imaging probe (Cy-prostate-PGC) within the tumor. Cleavage with specific enzyme allows the spatial separation of fluorochromes. The cleaved probe demonstrates high signal. Uptake within tumors in vivo is comparable to the uptake of tumor target-directed. The CNRs for prostate tumor-to-non-target tissue progressively increased during 15 mins observation period. The CNR value of prostate tumor 15 minutes after injection was 45.06±8.56. There are considerable CNR values for tumor-to-non-target tissue ratios. Moreover, the current imaging has an acceptable resolution and detection threshold.

In conclusion, the result of HPLC elution chromatography indicates that one major cut of the prostate peptide substrate in the presence of PSA was observed and two fragments are eluted. Since the control peptide is not a substrate of PSA, the control peptide remains intact and elutes at the original time. In addition, following the addition of PSA, the NIRF signal of prostate peptide substrate probe enhances 5-fold within 35 minutes; this is a significantly greater activation than that of control probe. In vitro signal intensity of optical imaging for Cy-prostate-PGC solution after incubation with PSA enhances significantly. Finally, in vivo imaging of the prostate tumor indicates that this near-infrared fluorochrome has the potential to serve as an imaging reporter for PSA activation in vivo and for biological studies in animal models.

The following examples are described for illustration of the method, features and advantages of the present invention and not for limitation of the scope of the present invention.

The synthesis of near-infrared fluorescence probe (NIRF probe):

EXAMPLE 1

Preparation of Methoxy Poly(ethylene glycol) Nitrile (2)

25 g (5 mmole) of methoxy poly(ethylene glycol) is dissolved in 25 ml deionized water and put into a 250 ml flask. 0.5 g of potassium hydroxide is added into the mixtures in ice-bath (0-5° C.) and 4.3 ml of acetonitrile is slowly added and react for 2.5 hour. Sodium phosphate is added into the solution after reaction to regulate pH value to 7.0. 200 ml, 70 ml and 50 ml of dichloromethane are respectively used to extract it for three times. The organic layer is collected to precipitate out water by magnesium sulfate, filtered to collect liquid and precipitated to elute solid by ethyl ether. After filtration, the solid is vacuum dried to obtain 23.2 g white solid with a yield of 91.8%. $^1$H-NMR (200 MHz, CDCl$_3$), δ (ppm): 2.1 ppm (t, 4H, —CH$_2$CN), 3.3 ppm (s, —OCH$_3$), 3.5 ppm (s, —CH$_2$CH$_2$O—), $^{13}$C NMR (200MHz, CDCl$_3$), δ (ppm) 28.8, 70.5, 128.2. IR:2360cm$^{-1}$ (—CN).

EXAMPLE 2

Synthesis method of methoxypoly(ethylene glycol) amide (3)

23 g (4.6 mmol) of methoxypoly(ethylene glycol)nitrile is dissolved in 111.4 ml of hydrochloric acid and is stirred under vibration at room temperature for 48 hours. After reaction ended, the solution is diluted with 1000 ml de-ionized and extracted with 200 ml, 150 ml and 100 ml of dichloromethane respectively three times. The collected organic layer is washed with de-ionized water twice, eluted out water with sodium sulfate, filtered to obtain filtered solution so as to dry the solution by a reduced-pressure evaporator, and vacuum dried to obtain 20.7 g of product with a yield of 90.1%. $^1$H-NMR(200 MHz, CDCl$_3$), δ (ppm): 2.47 ppm (t, 4H, —CH$_2$CONH$_2$), 3.2 ppm (s, —OCH$_3$), 3.5 ppm (s, —OCH$_2$CH$_2$O—), IR:3424cm$^{-1}$(—NH$_2$), 1638 cm-1, (—CONH$_2$).

EXAMPLE 3

Synthesis method of methoxypoly(ethylene glycol) propionic acid (4)

16 g (3.2 mmole) of methoxypoly(ethylene glycol)amide is solved into 1000 ml of de-ionized water. At room temperature 100 g (1.79 mole) of potassium hydroxide is added into the resulting solution to react for 22 hours. After reaction, 150 g (1.91 mole) sodium chloride is added. The solution is extracted by 150 ml dichloromethane for three times. The organic layer is collected, washed with 5% oxalic acid and de-ionized water and eluted out water with sodium sulfate. The solution is filtered and precipitated by ethyl ether to obtain solid. The solution is filtered to be vacuum dried to obtain 13.7 g of product with a yield of 85.8%. $^1$H-NMR(200 MHz, CDCl$_3$), δ (ppm): 2.5 ppm (t, 4H, —CH$_2$COOH), 3.2 ppm (s, —OCH$_3$), 3.5 ppm (s, —OCH$_2$CH$_2$O—), $^{13}$C NMR (200 MHz, CDCl$_3$), δ (ppm) 30.7, 39.5, 39.7, 69.8, 206.5. IR: 3453 cm$^{-1}$ (—OH).

EXAMPLE 4

Methoxy-polyethylene glycol succinimidyl propionic acid, MPEG-SPA (5)

3.4 g (1 mmole) of methoxypoly(ethylene glycol)propionic acid is dissolved in 20 ml of dichloromethane and 0.24 g of N-hydroxysuccinimide (2.1 mmole) to react in ice-bath (0° C.). 2.1 mmole of dicyclohexylcarbodiimide dissolved in 4 ml of dichloromethane is dissolved in the solution. After reaction, the solution is vibration stirred overnight at room temperature, eluted out solid by precipitation of ethyl ether, filtered to be vacuum dried to obtain 3.2 g of product with a yield of 92.1%. $^1$H-NMR(400 MHz, CDCl$_3$), δ (ppm): 2.81 ppm (t, 4H, —NHS), 2.92 ppm (t, 4H, —CH$_2$—COO—), 3.2 ppm (s, —OCH$_3$), 3.5 ppm (s, —OCH$_2$CH$_2$O—), $^{13}$C NMR (400 MHz, CDCl$_3$), δ (ppm) 25.2, 25.3, 31.2, 58.8, 69.9, 71.1, 72.3, 166.7, 168.8, 169.4. Anal. Calcd.(found)C$_{16}$H$_{29}$N$_3$O$_9$: C, 55.23 (54.42); H, 9.1 (9.17); N, 19.43 (19.25).

EXAMPLE 5

Synthesis Method of Prostate Peptide Substrate and Control Peptide

Preparation of Peptide Sequence (1):

In order to synthesize a peptide by using a peptide synthesizer (PS3, Rainin Instrument Co. Inc.), 156 mg (0.1 mmole) of Rink Amide resin is put into a reaction flask, 5 ml of dimethylformamide is poured into it to collect the resin at the bottom of the reaction flask and a stirring time of nitrogen is set at 30 minutes. Each species of amino acids is weighted for a amount of 0.4 mmole and respectively put into each of 11 vials of amino acids on which the name of the amino acid is marked. An same equivalent amount (208 mg, 0.4 mmole) of benzotriazole-1-yl-oxy-tris-pyrrolidino-phosphonium hexafluorophosphate is (PyBOP) is added into each of the 11 vials. Each vial is put on a wheel from location no. 3 to 13 in the direction of C-terminal to N-terminal. Each of amino acid sequences of a prostate peptide substrate and control peptide of it and a weighted amount of it are run. For the vials at location no. 3 to 12 a amino acid protection group has been chosen to be Fmoc and for N-terminal a protection group has been chosen to be Boc. After entering a main menu system of the PS3, "1", is selected and enter into EDIT and RUN icon to set a synthesis parameter PRG 03 (single coupling, pre-detach the protection group). A DEP icon by using a 20% piperidine indicating N-terminal protection group detachment for two times (5 minutes/run) is set up. The vials are dissolved by an amino acid coupling reagent NMM (N-methyl morphine) and is activated (ACT icon) by mixing for 30 seconds. The resin is coupled and stirred (AA icon) with each of the amino acids for 2 hours to press RUN key to start the synthesis. After each of the reactions ends, some of the resin is taken to carry out Kaiser test assay. 7.5 μl of ninhydrin and 10 μl of phenol are added to react at a temperature from 110 to 120° C. for three minutes. If yellow color exhibits, it represents that the protection group exists. For all the reactions when the last amino acid vial (at location no. 13) precedes the reaction, it implies that the synthesis is completed and the PAUSE key is pressed twice to temporarily stop the reaction. The Exit key is pressed and return to the MAIN menu to choose to press "2" MANUAL OPERATION key or to choose to press "3" REACTION VESSEL CONTROL key. The reaction flask is taken out. The resin is washed by ethyl alcohol, wash by dichloromethane, filter it, and vacuum dry it.

To Remove a Protection Group on a Branch Linkage Dde of Lysine (2):

0.2 ml of hydrazine is dissolved into 10 ml of dimethylformamide to a concentration of 2% and reacted with resin for 3 minutes. The above washing step is repeated twice. After the reaction is completed, Kaiser test assay is carried out and the resin exhibits blue color representing that the branch linkage Dde is de-protected completely. The resin is filtered in a filtering flask and washed with ethyl alcohol and with dichloromethane. The resin is filtered and dried under vacuum.

FITC is Bound to Branch Linkage of Lysine (3):

155.8 mg (0.4 mmole) of FITC is reacted with the resin and dissolved into 1 ml of dimethyl sulfoxide and 4 ml of diisopropylethylamide. Then, the mixture is vibration stirred at room temperature for 24 hours. After the reaction ends, Kaiser test assay is carried out and the resin exhibits deep yellow color representing that FITC is bound to it. The resin is washed with ethyl alcohol and dichloromethane, filtered and dried under vacuum.

To Cut a Protection Group at Branch Linkage of Amino Acid Sequence (4):

5 ml of arranged cutting reagent and protection group removing solution of trifluoroacetic acid/water/1,2-ethandithiol/triethylsilicone of 94.5/2.5/2.5/1 are mixed with 0.1 g of a resin. The resulting mixture is vibration stirred for 2.5 hours to react. The resin is washed with ethyl alcohol, filtered. The filtered liquid is collect and dried in a depressed vacuum evaporator. Ethyl ether is added drop by drop to precipitate in ice bath. The liquid is separated by a centrifugal machine for about 5 minutes with a rotation rate of 6000 rpm to separate a solid and a liquid. The above step is repeated by washing with diethyl ether for 3 to 5 times. The diethyl ether is vacuum dried to obtain a yellow solid which is the prostate peptide sequence. The solid is dried under vacuum to obtain a product of 129.4 mg with a yield of 83%.

Peptide Purity Analysis (5):

1 mg of the peptide sequence obtained is dissolved into 1 ml of methyl alcohol and its purity is analyzed by using a HPLC. The mobile phase of the prostate peptide substrate arranged is used as an eluent solution. Its ESI-MS (MH$^+$): prostate peptide substrate, 1563.66 (calcd), 1563.62 (found); control peptide, 1563.66 (calcd), 1563.64 (found).

EXAMPLE 6

Synthesis Method of Prostate Near-Infrared Fluorescence Probe, NIRF Probe) (4)

The synthesis of the NIRF probe is shown in Scheme 3.

Preparation of Protected Graft Copolymer (PGC) (1):

50 mg (3.4 mmole) of poly-L-lysine (PL) is dissolved into 12.5 ml of sodium bicarbonate solution (0.1M, pH 8.0) and 397.5 mg (79.5 mmole) of MPEA-SPA is slowly added. The solution is homogeneously mixed and its pH value is regulated to 7.7 by using sodium hydroxide. The solution is vibration stirred at room temperature for 3 hours and filtered by ultrafiltration by YM-3 membrane. The upper layer is lyophilized to obtain 50.8 mg of cotton-wool-like protected graft copolymer (PGC). 2,4,6-trinitrobenzene sulfonic acid (TNBS) is used to analyze the amount of free amino group.

Preparation of Iodoacetylate Protected Graft Copolymer (2):

7.5 mg (0.1 mmole) of protected graft copolymer (PGC) is dissolved into 0.2 ml of sodium bicarbonate (50 mM). and an access amount of iodoacetic acid anhydride (26.3 mg, 10 mmloe) is dissolved into 0.1 ml of dimethylformamide. After homogeneous mixing, the solution is iodoacetylated, reacted for 3 hours at room temperature, and after centrifugal ultrafiltered by using YM-3 membrane. The upper layer is lyophilized to obtain 7 mg of cotton-wool-like iodoacetylate protected graft copolymer (IA-PGC). Trinitrobezene sulphonic acid is used to analyze and the assay result indicates transparent color representing no existence of free amino group.

EXAMPLE 7

Preparation of Peptide Protected Graft Copolymer (P-PGC) (3)

5 mg of iodoacetylate protect graft copolymer (IA-PGC) is added into a buffer solution (0.1M, pH 6.5) of 0.2 ml of acetonitrile and 0.2 ml of sodium acetate containing 3.2 mg (2 mmol) of peptide substrate and 3.2 mg (2 mmol) of control peptide to react for 3 hours. Using Sephadex G-25 (20 cm×1 cm) for purification, the eluent solution is a phosphate buffer solution (10 mM, pH 7.0). To collect by a fractional collector, for each test tube 2 ml of liquid is collected. The absorption for each test tube at a wavelength of 494 nm is measured by a UV/Vis optical spectrum analyzer. The amount of test tubes is drafted to be the abscissa and the absorption value is drafted to be the ordinate to obtain a drawing. The first absorption peak which is large molecular weight is the peptide protected graft copolymer. The collected liquid is lyophilized to obtain a protected graft copolymer of needle-like peptide substrate and control peptide (57 mg and 27.6 mg).

Preparation of Prostate Near-Infrared Fluorescence Probe (NIRF Probe) (4):

0.5 mg of peptide protected graft copolymer (P-PGC) is dissolved into 0.2 ml of 50 mM sodium bicarbonate and 1 mg of Cy5.5 dye (1 mmol) is reacted with it. After homogeneous mixing, the mixture is vibration stirred for 1 hour at room temperature. After centrifugal, it is ultrafiltered by using YM-3 membrane. The upper layer is lyophilized to obtain a blue solid probe.

The Substitute Sequence Listing filed Apr. 17, 2007, and re-submitted on Oct. 5, 2007 in the text file "Substitute_Sequence_Listing_2-2_Amended_Apr._17 _2007" is incorporated by reference herein as if fully set forth. The text file containing the Substitute Sequence Listing was created Apr. 17, 2007 and is 6.58KB in size.

What is claimed is:

1. A prostate peptide substrate having the following formula:

Gly-Hyp-Ala-Ser-Chg-Gln-Ser-Leu-Met-Lys(FITC)-Cys-NH$_2$ [SEQ ID NO: 8]

wherein, Hyp is hydroxyproline, Chg is cyclohexyiglycine, and FITC is Fluorescein isothiocyanate.

2. A peptide substrate probe having the following formula (I):

B-Gly-Hyp-Ala-Ser-Chg-Gln-Ser-Leu-Met-Lys(FITC)-Cys-P [SEQ ID NO: 9]     (I)

wherein,

B is one selected from the group consisting of Cy5.5, Cy5, Cy7 and Alexa 750, Alexa 660, Alexa 680, IR 800, a lanthanide series metal complex and a near-infrared fluorescence dye, P is one selected from the group consisting of a polysaccharide, a polylysine, a polyethylene imine and a synthetic polymer;

Hyp is hydroxyproline,

Chg is cyclohexylglycine, and

FITC is Fluorescein isothiocyanate.

3. A prostatic cancer probe comprising a prostate peptide substrate of claim 1.

* * * * *